(12) United States Patent
Anderson et al.

(10) Patent No.: US 6,841,167 B1
(45) Date of Patent: Jan. 11, 2005

(54) β-CARBOLINE PHARMACEUTICAL COMPOSITIONS

(75) Inventors: Neil R. Anderson, West Lafayette, IN (US); Rampurna P. Gullapalli, Elmsford, NY (US)

(73) Assignee: Lilly Icos LLC., Wilmington, DE (US)

( * ) Notice: Subject to any disclaimer, the term of this patent is extended or adjusted under 35 U.S.C. 154(b) by 0 days.

(21) Appl. No.: 10/031,531

(22) PCT Filed: Apr. 26, 2000

(86) PCT No.: PCT/US00/11136

§ 371 (c)(1),
(2), (4) Date: Apr. 15, 2002

(87) PCT Pub. No.: WO01/08687

PCT Pub. Date: Feb. 8, 2001

Related U.S. Application Data

(60) Provisional application No. 60/146,924, filed on Aug. 3, 1999.

(51) Int. Cl.[7] .............................. A61K 9/48; A61K 9/64; A61K 9/66

(52) U.S. Cl. ........................ 424/456; 424/451; 424/452; 424/455

(58) Field of Search .................................. 424/451, 452, 424/455, 456

(56) References Cited

U.S. PATENT DOCUMENTS 5,294,615 A * 3/1994 Meyer et al. ........... 514/252.17

FOREIGN PATENT DOCUMENTS

| EP | 0 649 651 A1 | * 4/1995 | |
|---|---|---|---|
| EP | 0 649 651 | 4/1995 | ............ A61K/9/48 |
| WO | WO 96/38131 | 12/1996 | ............ A61K/9/14 |
| WO | WO 97/03675 | * 2/1997 | |
| WO | WO 99/30697 | * 6/1999 | |
| WO | WO 00/53148 | 9/2000 | |
| WO | WO 00/66099 | * 11/2000 | |
| WO | WO 00/66114 | * 11/2000 | |

* cited by examiner

*Primary Examiner*—Thurman K. Page
*Assistant Examiner*—S. Tran
(74) *Attorney, Agent, or Firm*—Marshall, Gerstein & Borun LLP

(57) ABSTRACT

A soft capsule containing a solution or suspension of a PDE5 inhibitor, and use of the capsule in treating sexual dysfunction.

14 Claims, No Drawings

β-CARBOLINE PHARMACEUTICAL COMPOSITIONS

CROSS-REFERENCE TO RELATED APPLICATIONS

This is the U.S. national phase application of International Application No. PCT/US00/11136, filed on April 26, 2000, which claims the benefit of provisional patent application Ser. No. 60/146,924, filed Aug. 3, 1999.

FIELD OF THE INVENTION

This invention relates to the fields of pharmaceutical and organic chemistry involving β-carboline compounds that are useful in the treatment of various medical indications where inhibition of type 5 cGMP-specific phosphodiesterase is desired. More particularly, β2-carboline compounds are formulated in a manner providing uniform potency, and desirable stability and bioavailability characteristics.

BACKGROUND OF THE INVENTION

The biochemical, physiological, and clinical effects of cyclic guanosine 3', 5'-monophosphate specific phosphodiesterase (cGMP-specific PDE) inhibitors suggest their utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle, and its expression in penile corpus cavernosum has been reported (A. Taher et al., *J. Urol.,* 149, pp. 285A (1993)).

Thus, PDE5 is an attractive target in the treatment of sexual dysfunction (K. J. Murray, *DN&P* 6(3), pp. 150–56 (1993)).

Daugan U.S. Pat. No. 5,859,006 discloses a class of β-carbolines, and pharmaceutical compositions thereof, which are useful in the treatment of conditions where inhibition of PDE5 is desired.

Also, see PCT publication WO 97/03675 disclosing the use of such β-carbolines for the treatment of sexual dysfunction.

The poor solubility of many β-carbolines a useful as PDE5 inhibitors has prompted the development of coprecipitate preparations, as disclosed in Butler U.S. Pat. No. 5,985,326. Briefly described, coprecipitates of β-carbolines with a polymer, e.g., hydroxypropyl methylcellulose phthalate, were prepared, then milled, mixed with excipients, and compressed into tablets for oral administration.

However, studies revealed some difficulties in generating precisely reproducible lots of coprecipitate product, thereby making the use of coprecipitates less than ideal for pharmaceutical formulations.

In addition, clinical studies involving administration of tablets containing such a coprecipitate preliminarily revealed that maximum blood concentration of the β-carboline is achieved in 3 to 4 hours, with the average time for onset of a therapeutic effect not yet precisely determined. When used for the treatment of sexual dysfunction, such as male erectile dysfunction or female arousal disorder, a more rapid attainment of maximum blood concentration, along with a greater prospect for rapid onset of therapeutic effect, is desired by patients, who prefer more immediate effects. Accordingly, there is a continuing need in the art for oral dosage forms of β-carbolines, and pharmaceutical compositions thereof, useful in the treatment of conditions where inhibition of PDE5 is beneficial.

SUMMARY OF THE INVENTION

This invention provides pharmaceutical formulations comprising a compound of structural formula (I):

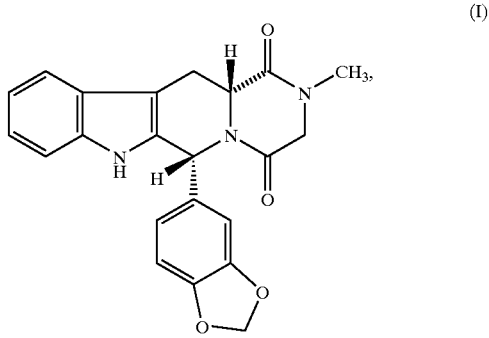

(I)

named (6R-trans)-6-(1,3-benzodioxol-5-yl)-2, 3, 4, 7, 12, 12a-hexahydro-2-methylpyrazino-[1', 2':1, 6]pyrido[3,4-b]indole-1,4-dione, and alternatively named (6R,12R)-2,3,6, 7,12,12a-hexahydro-2-methyl-6-(3,4-methylenedioxyphenyl)-pyrazino[[2', 1':6, 1]pyrido-3,4-b]indole-1,4-dione, and pharmaceutically acceptable salts and solvates thereof, wherein the compound preferably is provided as a free drug either dissolved or suspended in a pharmaceutically acceptable solvent, and the resulting solution or suspension is encapsulated in a soft capsule shell.

A preferred pharmaceutical composition comprises about 1% to about 45% by weight of the compound of structural formula (I), preferably provided as free drug, either dissolved or suspended in a pharmaceutically acceptable solvent. The composition is encapsulated in a soft shell, such as a gelatin shell, in a sufficient amount to provide an oral dose of the compound of structural formula (I) of about 1 to about 20 mg, preferably about 2 to about 20 mg, more preferably about 5 to about 20 mg, and most preferably about 5 to about 15 mg. A particularly preferred soft capsule of the present invention contains a 5 mg or a 10 mg oral dose of the compound of structural formula (I).

The present invention further relates to the use of such capsules for treatment of sexual dysfunction, e.g., male erectile dysfunction and female arousal disorder.

DETAILED DESCRIPTION OF THE INVENTION

For purposes of the invention disclosed and claimed herein, the following terms and abbreviations have the following meanings.

The term "treatment" is defined to include preventing, lowering, stopping, or reversing the progression or severity of a condition or symptom being treated. As such, the present invention includes both medical therapeutic and/or prophylactic administration, as appropriate.

The term "effective amount" is an amount of a pharmaceutical composition that is effective in treating the target condition or symptom. An effective of amount of the compound of structural formula (I) to treat sexual dysfunction in a male is an amount sufficient to provide and sustain an erection capable of penetrating his partner. An effective amount of the compound of structural formula (I) to treat female sexual dysfunction, particularly female arousal disorder, is an amount sufficient to enhance the patient's ability to achieve or sustain an aroused state.

The term "free drug" refers to solid particles consisting essentially of the compound of structural formula (I), as opposed to the compound intimately embedded in a polymeric coprecipitate.

The term "suspending agent" refers to a compound or composition that prevents or retards the settling of solid particles of the compound of structural formula (I) from a liquid suspension of the particles.

The term "suspension" refers to solid particles of the compound of structural formula (I) dispersed in a liquid carrier.

The term "solvate" refers one or more molecules of a solute associated with a molecule of a compound, such as the compound of structural formula (I) associated with a molecule of water or acetic acid.

The term "surfactant" refers to nonionic surfactants. Nonlimiting, representative surfactants include polysorbate 20, polyoxy 40 hydrogenated castor oil, and tocophersolan (d-α-tocopheryl polyethylene glycol 1000 succinate).

The term "solid oral dosage form" is used in a general sense to refer to pharmaceutical products administered orally. General oral dosage forms are recognized by those skilled in the art to include such forms as tablets and capsules, for example.

The nomenclature describing the particle size is commonly referred to herein as the "d90." A d90 of 40 means that at least 90% of the particles have a particle size less than 40 microns.

As previously stated, the present invention provides pharmaceutical formulations containing the compound of structural formula (I), as disclosed in Daugan U.S. Pat. No. 5,859,006, and pharmaceutically acceptable salts and solvates thereof. A preferred solvent suitable to prepare such a compound includes acetic acid.

Applicants have found that dosage uniformity, stability, and bioavailability are enhanced by formulating (6R-trans)-6-(1,3-benzodioxol-5-yl)-2,3,6,7,12,12a-hexahydro-2-methylpyrazino-[1', 2':1, ]pyrido[3,4-b]indole-1,4-dione (referred to herein as Compound A) with a pharmaceutically acceptable solvent, and incorporating the resulting solution or suspension into a soft shell to provide a capsule of the present invention.

The total amount of active compound in the pharmaceutical formulation is about 1% to about 45%, preferably about 2% to about 20%, by weight of the formulation. The active compound used in the present invention can be made according to established procedures, such as those detailed in Daugan U.S. Pat. No. 5,859,006, incorporated herein by reference.

For capsules containing a dispersion of Compound A, the particle size of the active compound has been found to enhance the bioavailability and handling of the present formulations. Thus, the particle size of the compound of structural formula (I) prior to formulation is controlled by milling the raw drug (as a crystal, amorphous precipitate, or mixture thereof) such that at least 90% of the particles have a particle size of less than about 40 microns (d90=40), and preferably less than about 30 microns. More preferably, at least 90% of the particles have a particle size of less than about 25 microns, still more preferably, less than about 15 microns, and most preferably, less than about 10 microns.

Methods for determining the size of particles are well known in the art. The following nonlimiting method, disclosed in U.S. Pat. No. 4,605,517, incorporated herein by reference, can be employed. In particular, the laser scattering particle size distribution analysis is effected on a small sample of the reduced material which is suspended in approximately 180 ml of dispersant solution. The sample is added to the dispersant until an acceptable level of laser light obscuration is achieved, at which point the particle size distribution is measured. Prior to the sample suspension, the dispersant solution is prepared by preparing a solution of 0.1% SPAN 80 (sorbitan oleate) in cyclohexane which is presaturated with the compound. The dispersant solution is filtered through a 0.2 micron microporous membrane filter to provide the necessary particle-free suspending dispersant. Triplicate measurements are effected as a minimum (a) to produce more reliable measurements, and (b) to check the equivalent sampling of the suspended material. The results are automatically recorded and displayed graphically to give a cumulative % undersize vs. diameter, and a frequency percentage vs. diameter for the sample. From this data, the median equivalent spherical volume diameter value and d90 are derived (90% undersize value) together with the standard deviation of the distribution calculated as above.

A formulation of the present invention is a suspension or solution filled in soft capsules, such as gelatin capsules. Such capsules often are referred to as "soft elastic capsules" (SEC) or "softgels" by persons skilled in the art. Capsule formulations are especially preferred for an active compound having a low solubility, such as the compound of structural formula (I). For example, Compound A has a water solubility of about 2 μg (micrograms) per milliliter of water at 25° C. Compounds having a low solubility have demonstrated a low and inconsistent bioavailability. Soft gelatin capsules containing a solution or suspension of the low solubility compound of structural formula (I) have overcome problems associated with drug bioavailability, while providing an oral dosage form preferred by patients.

The specific dose of Compound A administered according to the present invention is determined by the particular circumstances surrounding the case including, for example, the dosage form, the route of administration, the state of being of the patient, and the pathological condition being treated. A typical daily dose is about 1 to about 20 mg/day of the compound of structural formula (I). Preferred daily doses generally are about 2 to about 15 mg/day, and particularly about 5 mg or about 10 mg doses, administered once per day. Multiple doses can be taken to achieve a total dose of up to about 20 mg/day of the compound of structural formula (I). The selection of a particular dose is decided by the attending physician.

The present invention is particularly directed to an improved solid oral dosage form for a PDE5inhibitor, in particular for a PDE5 inhibitor having a low water solubility, such as Compound A. The improved dosage form can be used to treat sexual dysfunction, particularly male erectile dysfunction and female arousal disorder.

The improved solid oral dosage form is soft capsules, such as soft gelatin capsules, comprising a shell that encapsulates a solution or suspension of Compound A. In accordance with the present invention, the soft capsules are a solid dosage form in which a drug is encapsulated in a soft container or shell comprising a suitable form of gelatin. Gelatin possesses unique properties which make gelatin the primary material for the manufacture of soft capsule shells over other capsule shell materials, such as methylcellulose and calcium alginate.

Soft capsules provide advantages over other solid dosage forms, such as tablets. For example, many patients prefer capsules because capsules are easier to swallow. Thus, capsule forms of a drug often are made available in addition to tablet forms.

A soft capsule, or softgel, has a soft, globular, gelatin shell, typically plasticized by the addition of glycerin, sorbitol, or a similar polyol. The shell is filled with a suspension or solution of the compound of structural formula (I). The size and shape of the gelatin shell can vary widely. The shell, therefore, can be spherical, oval, oblong, or tube shaped, for example. The size of the capsule is related to the dose level of the drug encapsulated by the shell, and to the solubility and dispersability of the drug in the pharmaceutically acceptable solvent or carrier for the drug.

A soft capsule for an oral dosage of a drug typically is prepared such that a seam in the gelatin shell, or the shell itself, ruptures to release the drug solution or suspension within five to ten minutes after ingestion. Manufacture of the soft gelatin shell to encapsulate the drug suspension or solution is performed in accordance with methods well known in the art.

Compound A has an extremely low solubility in water of about 2 µg/ml, and has demonstrated a low and inconsistent bioavailability. Although Compound A is relatively insoluble in water, it is readily soluble in a variety of organic solvents, such as dimethylformamide and dimethyl sulfoxide. However, such solvents are not pharmaceutically acceptable. The present invention is directed to a formulation for filling a soft gelatin shell, and thereby providing a soft capsule that is both physically and chemically stable, and allows the manufacture of capsules having the smallest possible size. As described hereafter, a solution formulation and a suspension formulation were prepared to provide a soft capsule having a gelatin shell encapsulating an effective dose of Compound A.

The following formulation examples are illustrative only and are not intended to limit the scope of the present invention.

EXAMPLE 1

Capsules Containing a Solution Formulation

The solubility of Compound A was determined in various pharmaceutically acceptable solvents. These solvents included hydrophilic solvents, such as polyethylene glycol 400 (PEG 400), propylene glycol, and glycofurol, and lipophilic solvents, such as triethyl citrate, propylene glycol mono- and dilaurate, and medium chain ($C_8$ and $C_{10}$) mono-, di-, and triglycerides. The solubility studies showed that Compound A has an extremely low solubility in lipophilic solvents.

The solubility of Compound A in hydrophilic solvents was determined by dissolving increasing amounts of Compound A, i.e., 2% to 5% by weight, in a pharmaceutically acceptable solvent, e.g., PEG 400, alone or in the presence of povidone (i.e., a medium molecular weight polyvinylpyrrolidone (PVP)) at 60±5° C. The solutions then were allowed to cool to room temperature (RT). A portion of each solution was mixed with water (8 mg water per 100 mg solution) to mimic the water migration and retention processes occurring in a soft capsule. The solutions (with and without water) were stored at RT (room temperature) and at 4° C. for physical stability evaluation. In this evaluation, the solutions were observed under a microscope at regular intervals for the presence of drug crystals.

The physical stability evaluation showed that compositions containing 2% to about 2.8% by weight of Compound A, 5% by weight of propylene glycol, and the remainder PEG 400 were stable in that no crystals of Compound A were observed after 120 days of storage. The solubility study of Compound A in PEG 400 indicated that a solution formulation of Compound A was physically stable with respect to drug crystallization at room temperature and at 4° C. at about 2.8% or lower drug concentrations. Accordingly, 25 mg of Compound A can be encapsulated in a gelatin shell at a 900 mg or greater fill weight.

A batch of soft capsules then was manufactured by encapsulating 900 mg of a PEG 400 solution containing 25 mg of Compound A in a gelatin shell. The capsules were manufactured using a standard gelatin formulation as the shell, with sorbitol and glycerin as the plasticizers and titanium dioxide as the shell opacifier. The encapsulation process was performed using an oblong, shallow body die, having a thickness of 0.22 inch, for the shell. This shell thickness provided a fast release of the solution formulation from the capsules, which results in a rapid absorption by a human body, and an expected rapid onset of action. The solution formulation and physical stability are summarized in the following table.

| Formulation | |
|---|---|
| Ingredients | mg/capsule |
| Filling Solution: | |
| Compound A | 25 |
| PEG 400 NF, LA[1] | 830 |
| Propylene glycol, USP | 45 |
| Fill Weight, mg | 900 |
| Fill moisture (%) Day 1  Day 2 | 6.86    6.76 |
| Hardness (Newtons) | 8.8     9.8 |
| Size/Shape | Oblong-Shallow body die |
| Capsule Shell Ingredients: | |
| Gelatin, Lime bone | |
| Glycerin | |
| Sorbitol | |
| Water, purified | |
| Titanium dioxide | |
| Shell Color | Opaque White |
| Physical Stability: | |
| Days | 120 |
| 4° C. | No Crystals |
| RT | No Crystals |

[1]polyethylene glycol 400, low aldehyde

The physical stability of the capsules of Example 1 was evaluated at room temperature and at 4° C. The chemical stability of the capsules also was evaluated at 25° C. and 60% relative humidity (real time conditions) and at 40° C. and 75% relative humidity (accelerated stability conditions). The dissolution profiles were measured using the USP Paddle method at 75 rpm in 1000 ml of 0.5% sodium lauryl sulfate solution at 37° C. ±0.5° C. The dissolution profiles and chemical stability data are summarized in the following tables.

| Dissolution Profile Results | | | | |
|---|---|---|---|---|
| Rupture Time | Average Dissolution (%) n = 6 | | | |
| min:sec | 10 min. | 20 min. | 30 min. | 60 min. |
| 1:17–8:08 | 97 | 99 | 99 | 99 |

| Chemical Stability Results | | | |
|---|---|---|---|
| Time & Conditions | Assay, % (n = 2) | Related Substances, % (n = 2) | Chiral Impurities, % (n = 2) |
| Initial | 98.6 | 0.15 | N/A |
| 40° C./75% RH 30 days | 99.1 | 0.15 | N/A |
| 40° C./75% RH 60 days | 98.7 | 0.40 | 0.30 |
| 40° C./75% RH 90 days | 98.6 | 0.60 | 0.45 |

-continued

| | | | |
|---|---|---|---|
| 40° C./75% RH | | | |
| 90 days | 99.5 | 0.40 | 0.10 |
| 25° C./60% RH | | | | n = number tested

The capsules of Example 1 showed that capsules containing 25 mg of Compound A were physically stable with respect to crystallization at room temperature and 4° C. for more than four months. Dissolution profiles, in 0.5% sodium lauryl sulfate solution, showed more than 80% of Compound A was dissolved within first 10 minutes, and dissolution was complete within the first 20 minutes.

In addition, no significant chemical degradation of Compound A was observed after storage of the capsules for three months under accelerated stability conditions. The total of related substances was as low as 0.6%, and the total chiral impurity was as low as 0.45%, in capsules stored under accelerated stability conditions for more than three months.

EXAMPLE 2

Capsules Containing a Suspension Formulation

Suspension formulations were investigated using a hydrophilic carrier (i.e., PEG 400) and
  a., using a lipophilic carrier (i.e., CAPMUL®MCM). CAPMUL®MCM is a mixture of medium chain ($C_8$–$C_{10}$) monoglycerides, available commercially from Capital City Products Co., Columbus, Ohio.

The suspensions were prepared by dispersing Compound A in a mixture of (a) a suspending agent, GELUCIRE® 44/14, and (b) either PEG 400 or CAPMUL® MCM. GELUCIRE® 44/14 is a blend of a saturated polyglycolyzed glycerides, available commercially from Gattefosse SA, Saint Priest, France. GELUCIRE® 44/14 and CAPMUL® MCM, separately, were premelted to about 60° C., then mixed to provide a suspension carrier. The carrier was allowed to cool to 40° C., then Compound A was dispersed in the carrier. Different ratios of GELUCIRE® 44/14 to CAPMUL® MCM or PEG 400 were studied to provide a suspension formulation that was easy to encapsulate below 35° C. and exhibited good dispersion (suspension) properties. The effect of incorporating a surfactant into the carrier, such as TWEEN® 20 (polysorbate 20), CREMOPHOR® RH 40 (PEG 40 hydrogenated castor oil), and vitamin E TPGS (tocophersolan), also was studied.

The suspensions were stored at room temperature, and evaluated by observation under a microscope at regular intervals for drug crystal growth in the suspension base. The suspensions were evaluated for physical stability in PEG 400 and CAPMUL® MCM over a concentration range of Compound A of 6.25% to 40%.

The studies on the suspension formulation in PEG 400 indicated that the formulation was physically stable with respect to Compound A sedimentation at room temperature. Suspension formulations containing CAPMUL® MCM and GELUCIRE® 44/14 as a carrier also demonstrated physical stability, and also exhibited better flow properties and dispersion in water than PEG 400-based formulations. In particular, compositions containing 6.25% Compound A; 5% propylene glycol; CAPMUL® MCM from 11.39% to 56.875%; and GELUCIRE® 44/14 from 31.875% to 74.67% were free flowing and showed a fair dispersion in water. The presence of a surfactant in the carrier had little to no effect on the formulations.

A formulation containing 6.25% Compound A, 5% propylene glycol, 44.375% CAPMUL® MCM, and 44.375% GELUCIRE® 44/14 was evaluated further. Using this formulation, 25 mg of Compound A was encapsulated at a 400 mg capsule fill weight.

A batch of soft capsules was manufactured by incorporating 400 mg of the above suspension formulation containing 25 mg Compound A in a standard soft gelatin shell having sorbitol and glycerin as shell plasticizers and titanium dioxide as the shell opacifier. The encapsulation process was performed using a oval shallow body die of 0.22 inch thickness.

Capsules containing the above suspension, and the physical and chemical stability of the capsules, are summarized in the following tables.

| Formulation | |
|---|---|
| Ingredients | mg/capsules |
| Filling Suspension: | |
| Compound A | 25.0 |
| CAPMUL ® MCM | 177.5 |
| GELUCIRE ® 44/14 | 177.5 |
| Propylene glycol, USP | 20.0 |
| Fill Weight, mg | 400 |
| Fill Moisture (%) Day 1  Day 2 | 3.17    2.17 |
| Hardness (Newtons) | 5.0    5.9 |
| Size/Shape | Oval - Shallow body die |
| Capsule Shell Ingredients: | |
| Gelatin, Lime bone | |
| Glycerin | |
| Sorbitol, special | |
| Water, purified | |
| Titanium dioxide | |
| Shell Color | Opaque White |
| Physical Stability: | |
| Days | 120 |
| 4° C. | No sedimentation |
| RT | No sedimentation |
| 40° C./75% RH | Sedimentation |

The physical and chemical stability of the capsules of Example 2 were evaluated using the criteria described in Example 1.

| Dissolution Profile Results | | | | |
|---|---|---|---|---|
| Rupture Time | Average Dissolution (%) (n = 6) | | | |
| min:sec | 10 min. | 20 min. | 30 min. | 60 min. |
| 0:40–1:39 | 63 | 82 | 90 | 96 |

| Chemical Stability Results | | | |
|---|---|---|---|
| Time & Conditions | Assay, % (n = 2) | Related Substances, % (n = 2) | Chiral Impurities, % (n = 2) |
| Initial | 96.5 | 0.15 | N/A |
| 40° C./75% RH 30 days | 97.4 | 0.05 | N/A |
| 40° C./75% RH 60 days | 97.1 | 0.10 | N/A |
| 40° C./75% RH | | | | n = number tested

The capsules of Example 2 demonstrated that soft capsules containing a suspension formulation incorporating 25 mg of Compound A were physically stable with respect to sediment formation at RT and 4° C. for more than four months. Slight settling of Compound A as a sediment was observed in capsules stored under accelerated stability conditions. In dissolution profiles, the suspension-filled capsules of Example 2 exhibited a total dissolution of Compound A in the dissolution medium beyond a 30-minute time period.

No significant degradation of Compound A was observed after two months storage when the capsules were stored under accelerated stability conditions. The total of related substances was as low as 0.1% in capsules stored under accelerated stability condition for two months.

EXAMPLE 3

Capsules Containing a Solution Formulation

The following is a soft gelatin capsule containing a 10 mg dose of a solution of Compound A.

| Ingredients | mg/capsules |
|---|---|
| Filling Solution: | |
| Compound A | 10 |
| PEG 400 NF, LA | 465 |
| Propylene glycol, USP | 25 |
| Fill Weight, mg | 500 |
| Fill moisture (%) Day 1 | 6.60 |
| Hardness (Newtons) | 7.7 |
| Size/Shape | Oval - Shallow body die |
| Capsule Shell Ingredients: | |
| Gelatin, Lime bone | |
| Glycerin | |
| Sorbitol, special | |
| Water, purified | |
| Titanium dioxide | |
| Shell Color | Opaque White |
| Physical Stability: | |
| Days | 60 |
| 4° C. | No Crystals |
| RT | NO Crystals |

The capsules of Example 3 exhibited an excellent dissolution profile and excellent chemical stability as demonstrated in the following tables.

| | Dissolution Profile Results | | | |
|---|---|---|---|---|
| Rupture Time | Average Dissolution (%) n = 6 | | | |
| min:sec | 10 min. | 20 min. | 30 min. | 60 min. |
| 3:40–5:39 | 95 | 98 | 99 | 101 |

| | Chemical Stability Results | | |
|---|---|---|---|
| Time & Conditions | Assay, % (n = 2) | Related Substances, % (n = 2) | Chiral Impurities, % (n = 2) |
| Initial 40° C./75% RH | 99.2 | 0.30 | 0 |
| 30 days 40° C./75% RH | 99.0 | 0.45 | 0.2 |
| 60 days 40° C./75% RH | 98.5 | 0.55 | 0.45 |

In addition to improved in vivo absorption, other important physical properties are dissolution and stability. The present soft capsules provide a fast-dissolving oral dose form having excellent stability.

The principles, preferred embodiments, and modes of operation of the present invention have been described in the foregoing specification. The invention that is intended to be protected herein, however, is not construed to be limited to the particular forms disclosed, because they are to be regarded as illustrative rather than restrictive. Variations and changes may be made by those skilled in the art without departing from the spirit of the invention.

What is claimed is:

1. A soft capsule comprising:

(a) a shell comprising gelatin, wherein said shell encapsulates (b) a suspension pharmaceutical formulation comprising about 1% to about 45% by weight of solid particles of an active compound having a structural formula

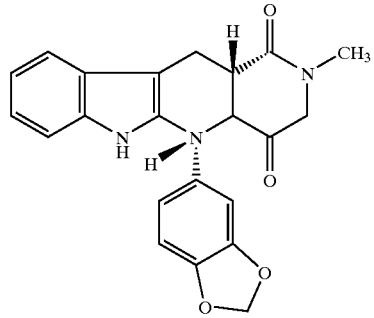

and a pharmaceutically acceptable carrier comprising (i) a pharmaceutically acceptable solvent selected from the group consisting of polyethylene glycol 400, propylene glycol, glycofurol, a $C_8$–$C_{10}$ monoglyceride, and mixtures thereof, and (ii) a suspending agent comprising a saturated polyglycolyzed glyceride.

2. The capsules of claim 1 wherein the active compound is present as a free drug.

3. The capsules of claim 1 wherein the pharmaceutically acceptable carrier further comprises a polyvinylpyrrolidone.

4. The capsules of claim 1 wherein the pharmaceutical formulation comprises about 2% to about 2.8% by weight of the active compound, about 3% to about 8% by weight propylene glycol, and about 90% to about 95% by weight polyethylene glycol 400.

5. The capsules of claim 1 wherein the solvent further comprises $C_8$–$C_{10}$ monoglycerides.

6. The capsules of claim 1 wherein the pharmaceutically acceptable carrier further comprises a surfactant.

7. The capsules of claim 5 wherein the pharmaceutical formulation comprises about 3% to about 8% by weight of the active compound, about 5% to about 8% by weight propylene glycol, about 10% to about 60% by weight of $C_8$–$C_{10}$ monoglycerides, and about 30% to about 75% by weight of a saturated polyglycolyzed glyceride.

8. The capsules of claim 1 wherein the active compound is present in an amount of about 1 to about 20 mg per capsule.

9. The capsules of claim 1 wherein the active compound is present in an amount of about 2 to about 20 mg per capsule.

10. The capsules of claim 1 wherein the active compound is present in an amount of about 5 to about 15 mg per capsule.

11. The capsules of claim 1 wherein the active compound is present in an amount of about 10 mg per capsule.

12. A method of treating sexual dysfunction in a patient in need thereof comprising administering to the patient a capsule of claim 1.

13. The method of claim 12 wherein the sexual dysfunction is male erectile dysfunction.

14. The method of claim 12 wherein the sexual dysfunction is female arousal disorder.

* * * * *

UNITED STATES PATENT AND TRADEMARK OFFICE
CERTIFICATE OF CORRECTION

PATENT NO. : 6,841,167 B1
DATED : January 11, 2005
INVENTOR(S) : Anderson et al.

Page 1 of 1

It is certified that error appears in the above-identified patent and that said Letters Patent is hereby corrected as shown below:

Column 1,
Line 17, "62" should be -- β --
Line 32, paragraph beginning "Thus, PDE5" is not a paragraph, this should be a continuation of the previous paragraph
Line 39, paragraph beginning "Also, see" is not a paragraph, this should be a continuation of the previous paragraph
Line 42, "a useful" should be -- useful --
Line 50, paragraph beginning "However, studies" is not a paragraph, this should be a continuation of the previous paragraph Column 2,
Line 59, "An effective of amount" should be -- An effective amount --

Signed and Sealed this

Seventh Day of June, 2005

JON W. DUDAS
*Director of the United States Patent and Trademark Office*